(12) United States Patent
Laufer et al.

(10) Patent No.: US 6,338,731 B1
(45) Date of Patent: Jan. 15, 2002

(54) METHOD AND SYSTEMS FOR REDUCING SURGICAL COMPLICATIONS

(75) Inventors: Michael D. Laufer, Menlo Park, CA (US); D. Bommi Bommannan, Los Altos, CA (US)

(73) Assignee: Ntero Surgical, Inc., Palo Alto, CA (US)

( * ) Notice: Subject to any disclaimer, the term of this patent is extended or adjusted under 35 U.S.C. 154(b) by 0 days.

(21) Appl. No.: 09/271,268

(22) Filed: Mar. 17, 1999

(51) Int. Cl.[7] .............................................. A61B 18/04
(52) U.S. Cl. ........................... 606/34; 606/41; 606/27; 606/20; 607/96; 607/100; 607/98; 604/20
(58) Field of Search ............................ 606/32, 34, 37, 606/39–42, 45, 46, 48–50, 20, 21, 22, 23, 27, 28, 31; 607/96, 98, 99, 100, 105; 604/19, 20

(56) References Cited

U.S. PATENT DOCUMENTS

| | | | |
|---|---|---|---|
| 5,213,580 A | 5/1993 | Slepian et al. | |
| 5,540,684 A | 7/1996 | Hassler et al. | |
| 5,690,675 A | * 11/1997 | Sawyer et al. | 606/229 |
| 5,711,958 A | 1/1998 | Cohn et al. | |
| 5,779,699 A | 7/1998 | Lipson | |
| 5,846,235 A | 12/1998 | Pasricha et al. | |
| 5,914,345 A | 6/1999 | Slepian et al. | |
| 5,944,718 A | * 8/1999 | Austin et al. | 606/48 |
| 5,992,418 A | * 11/1999 | de la Rama et al. | 128/898 |
| 6,004,547 A | * 12/1999 | Rowe et al. | 424/78.04 |
| 6,071,956 A | 6/2000 | Slepian et al. | |

* cited by examiner

*Primary Examiner*—Linda C. M. Dvorak
*Assistant Examiner*—R Kearney
(74) *Attorney, Agent, or Firm*—Pennie & Edmonds LLP

(57) ABSTRACT

Surgical complications can be minimized by reducing, or eliminating, the release of substances such as TGF-β from a surgical site by immediately sealing the edges of a surgically-made puncture or incision site. In one system, a treatment device includes an electrically conductive surface that is connected to a source of electrical energy and which can be placed in contact with the edge of a surgical incision or perforation site such that, when the conductive surface is electrically activated, it operates to heat the cellular material at the edge of the surgical incision or perforation site to inhibit (i.e., reduce) the formation of complicating connective tissue bridges. The source of electrical energy is, preferably, a radio-frequency generator.

27 Claims, 2 Drawing Sheets

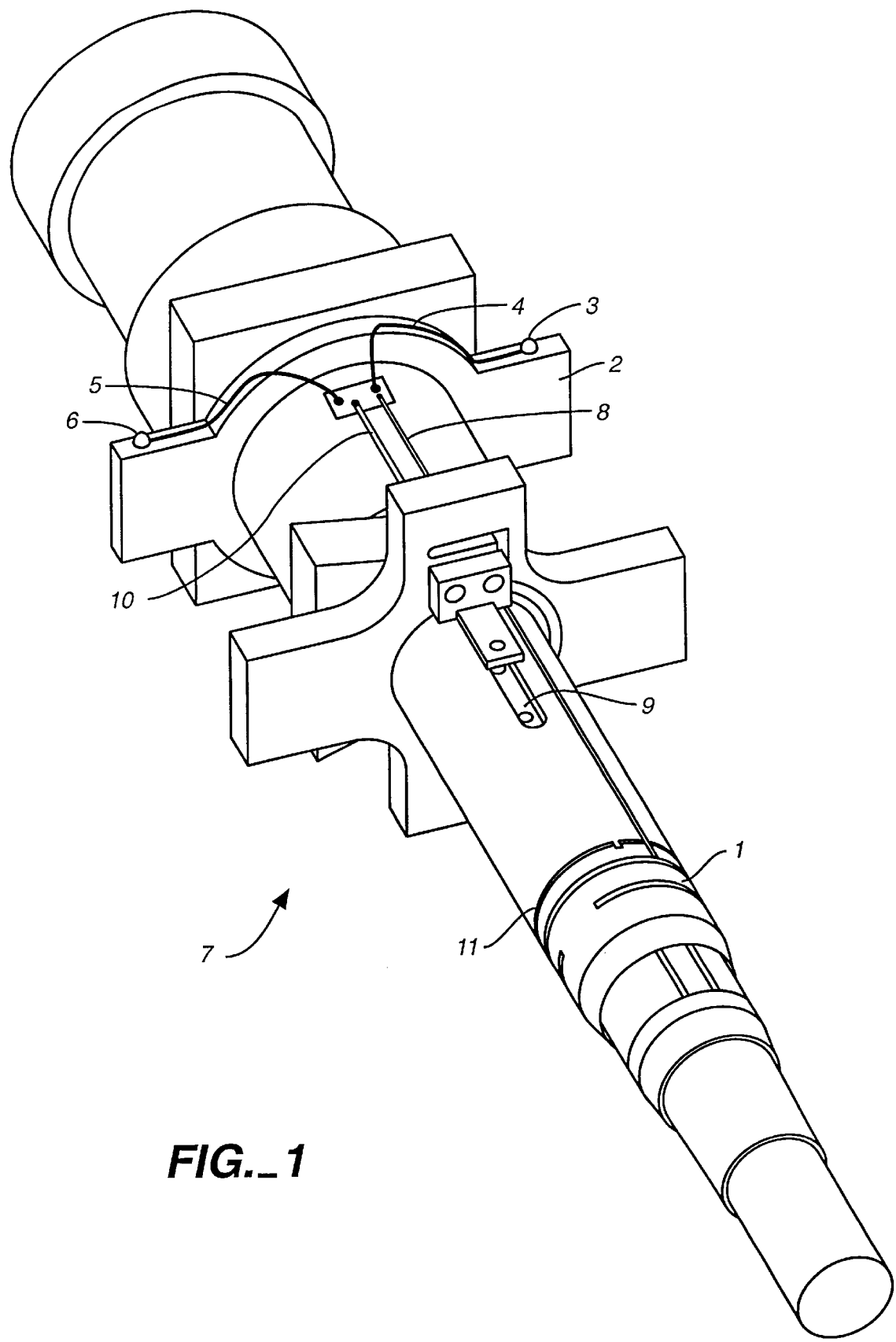
FIG._1

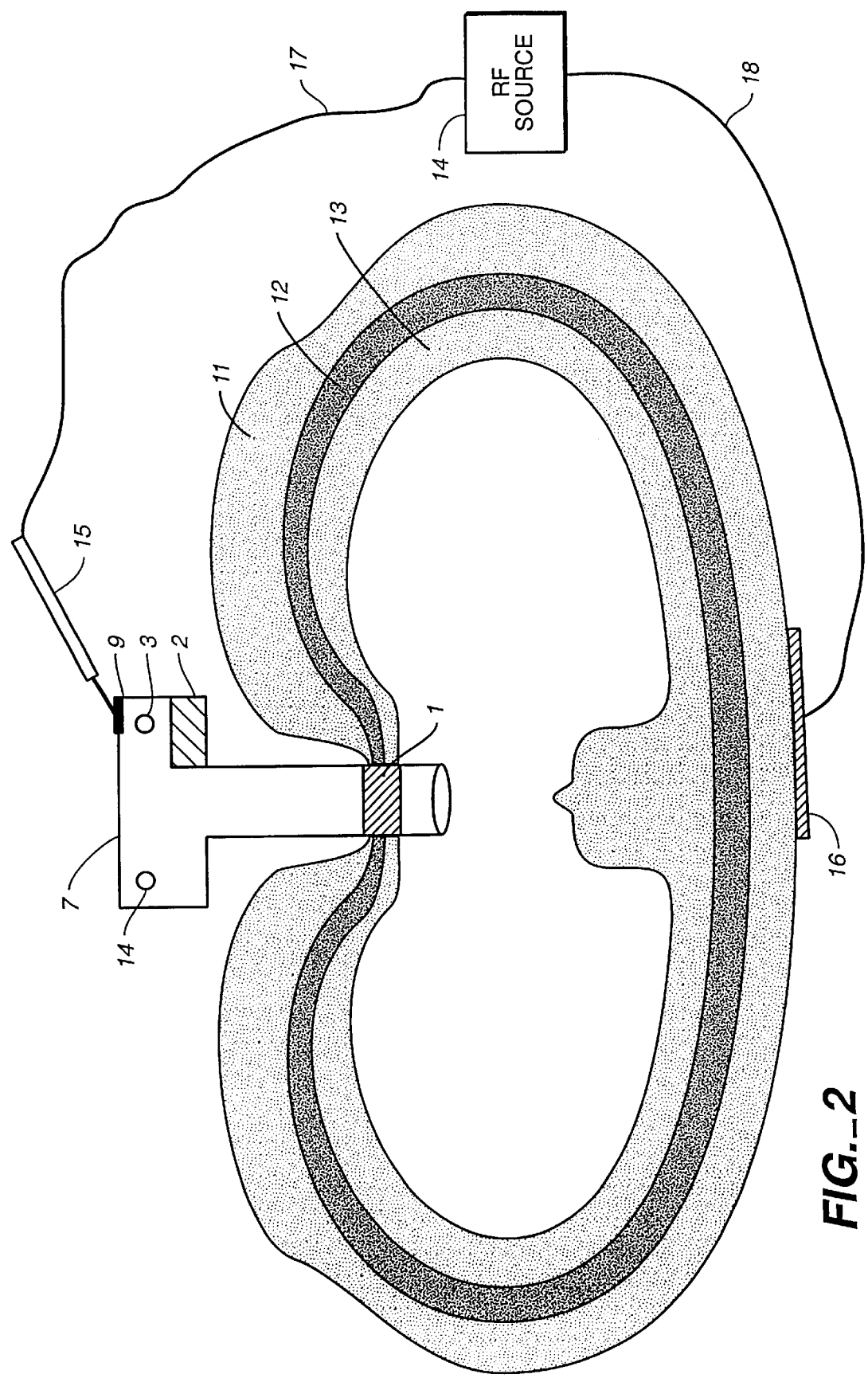
FIG._2

METHOD AND SYSTEMS FOR REDUCING SURGICAL COMPLICATIONS

BACKGROUND OF THE INVENTION

1. Field of the Invention

The present invention generally relates to systems for reducing the incidence of complications that occur following many surgical procedures within the chest or abdomen. More particularly, the present invention relates to systems for reducing post-surgical complications that occur due to the natural tendency of the human body to form adhesions between injured areas within body cavities.

2. State of the Art

As a result of the healing processes that follow chest and abdominal surgery, complications frequently arise due to the natural tendency of the human body to form adhesions, which are connecting tissue structures between injured areas within body cavities. Adhesions may form regardless of the nature of surgical procedures, whether done in a so-called minimally invasive fashion using laparoscopy or with a standard technique involving one or more relatively large incisions. A teleological explanation of adhesions is that they serve to limit the spread of infection from incidental stab wounds or perforations of body cavities. Regardless of their teleological purpose, however, these connective tissue bridges may cause various, often serious, complications. Usually the relief of post-surgical complications caused by adhesions requires another surgery. The subsequent surgery is complicated by the adhesions that were formed as a result of the previous surgery. The second surgery, itself, is likely to result in further adhesions and a continuing cycle of additional surgical complications.

One example of a problem that can be caused by adhesions is that, following abdominal surgery, loops of intestine may become entangled or twisted about these adhesions. The entanglements may cause partial or total flow obstruction through the bowel, or may compromise the blood flow to and from the bowel. If such a condition is not relieved rapidly, the bowel dies and shortly thereafter the condition causes death of the afflicted patient. As another example, adhesions that form in the pelvis after obstetric or gynecologic surgery may cause sterility as well as chronic pelvic pain.

Various suggestions have been made to avoid, reduce, or eliminate the formation of adhesions. For instance, standard surgical procedure in the United States often includes the steps of washing powder from surgical gloves prior to surgical operations, using powder-free gloves, and washing body cavities thoroughly prior to closing incisions. Another of the strategies that has been suggested to prevent adhesion formation is to loosely place a non-reactive barrier between an injured peritoneal surface and internal organs. Material such as Interceed™ and Seprafilm™ and methods as described in U.S. Pat. No. 5,791,352 to Reich et al., have been advocated for minimizing adhesions. Such procedures, however, have not been shown to be significantly effective in reducing the formation of adhesions.

It also has been suggested that injured tissue naturally releases many chemical messengers—including transforming growth factors—which are responsible, at least in part, for peritoneal healing. One of those factors, TGF-β, may stimulate the formation of adhesions. In other words, it has been postulated that, when the integrity of the abdominal lining (either peritoneum or pleura) is breached, the natural response is to release a substance such as TGF-β. Upon release, such substances initiate a healing process including forming connective tissue bridges (i.e., adhesions). To restrict the spread of TGF-β from injured tissue sites—and thus, possibly, to inhibit the formation of adhesions—barrier sheets have been developed. As mentioned above, Interceed™ and Seprafilm™ are examples of such barrier sheets that can be loosely layered in a non-sealing manner over injured tissue. Also, pourable substances have been suggested for scavenging TGF-β from injured tissue sites. These measures, unfortunately, have had only modest success in reducing the formation of post-surgical adhesions at the surgical locations. Therefore, it would be desirable to provide new and improved methods and apparatus that would eliminate of minimize adhesions.

SUMMARY OF THE PRESENT INVENTION

The present invention, generally speaking, provides systems for reducing adhesion formation by reducing, or eliminating, the release of chemical messengers such as TGF-β at a surgical location in a mammal. More particularly, the systems of the present invention provide, for example, electro-surgical instruments for use following abdominal surgery for substantially immediately sealing off the edges of surgically-made punctures or incisions in the peritoneum to, thereby, limit the release of factors such as the growth factor TGF-β following injury.

Generally speaking, the present invention provides a system for treating the edges of surgical incisions, or perforations, of the peritoneum for reducing the incidence of post-surgical adhesions, where the system includes means that are applied to, or act upon, the edges of the incised or perforated tissue of the peritoneum for sufficiently sealing the incised or perforated tissue to substantially reduce the incidence of post-surgical adhesions at the surgical site.

In one particular embodiment, the invention provides a system for sufficiently sealing the edges of incised or perforated tissue of the peritoneum to substantially reduce the incidence of post-surgical adhesions at the surgical site by heating the lymphatic tissue sufficiently to inhibit (i.e., reduce) the release of various factors and consequently inhibit or minimize the release of adhesion-producing substances such as growth factors. In one preferred practice with this embodiment, heat is produced by controlled radio-frequency energy for application to the edge of an incised or surgically injured peritoneal or pleural tissue. In practice, a wide variety of electromagnetic energy sources such as microwave, infrared, ultraviolet, optical (e.g., laser), and mechanical energy (e.g., ultrasound), could be used to generate heat.

In another particular embodiment, the invention provides a system for sufficiently sealing the edges of incised or perforated tissue of peritoneum to substantially reduce the incidence of post-surgical adhesions at the surgical site by cooling the edge of an incised or surgically injured peritoneal or pleural tissue sufficiently to inhibit (i.e. reduce) the release of adhesion-producing substances such as growth factors and consequently inhibit or minimize adhesion formation. In practice of this embodiment, cooling is accomplished by applying a low-boiling point liquid substance such as liquid nitrogen, Freon™ or the like to the edges of incised or perforated tissue.

In another particular embodiment, the invention provides a system for sufficiently sealing the edges of incised or perforated tissue of peritoneum to substantially reduce the incidence of post-surgical adhesions at the surgical site by applying a sealing substance at the site of injury. The sealing substance inhibits (i.e., reduces) the release of adhesion-producing substances such as growth factors and consequently inhibit or minimize adhesion formation. In practice of this embodiment, the sealing substance can be a biocompatable barrier material such as a cyanoacrylate liquid, or the like, that is applied to the edges of incised or perforated tissue. Other bio-compatible synthetic sealing materials could be polyvinyl resins, polylactate glycolides, polycaprolactones, poly oxyethylenes, and other such materials. One could also use biological materials such as proteins like collagen, gelatin, elastin, albumins, and the like, or mixtures thereof.

BRIEF DESCRIPTION OF THE DRAWINGS

The advantages of the present invention can be further understood by referring to the following detailed description in conjunction with the appended drawings, in which like numerals indicate similar elements and in which:

FIG. 1 is a perspective view of one preferred embodiment of a system according to the present invention; and FIG. 2 is a schematic, generally pictorial, representation of the system of FIG. 1 located at a surgical site within an abdominal wall.

DETAILED DESCRIPTION OF THE PREFERRED EMBODIMENT

As shown in FIG. 1, a system according to one embodiment of the present invention includes a conductive collar or sleeve 1 that is mounted to surround the neck section of a trocar generally indicated by numeral 7. The trocar 7 can be of generally conventional construction and, as such, has an elongated cylindrical distal section for insertion into a body cavity and a proximal end of enlarged diameter for manipulation by a surgeon. The conductive collar 1 is connected to a control system, generally indicated by numeral 2, which, for illustrative purposes, is shown as being physically mounted to the trocar 7.

In the embodiment shown in FIG. 1, the control system 2 is connected to a signal indicator means, such as a bulb 3 or LED indicator, by conductor 4. A signal bulb 6 is also electrically connected, as by conductor 5, to the control system 2. As further shown, the collar 1 is connected to the control means 2 by a conductor 8. Finally, a contact 9 is mounted on the trocar 7 and connected to the control means 2 as by conductor 10. The contact 9, in one embodiment, can receive radio-frequency energy from a conventional RF source (shown only in FIG. 2). A thermocouple 11 is placed adjacent to the collar 1 so that local tissue temperature can be measured. In operation of the control system, generally speaking, the indicator 3 is illuminated whenever the treatment is ongoing, and the signal bulb 6 is illuminated whenever the treatment is completed.

FIG. 2 shows the above-described system located within the tissues of an abdominal wall. In this schematic illustration, numeral 11 indicates the skin and muscle layer of the abdominal wall, numeral 12 refers to the connective tissue fascia, and numeral 13 indicates the peritoneal lining of the abdomen.

In conjunction with FIG. 2, one mode of operation of the above-described system can be understood to be practiced immediately following surgical intrusion into the abdomen, in order to reduce surgical complications. To provide context for the description of the operation of the system, FIG. 2 shows the position of the system substantially immediately after a surgeon has created an incision or perforation of the abdominal by insertion of the trocar 7 through the wall and into the abdominal cavity. Within a short period after that insertion, the surgeon adjusts the position of the trocar 7 such that the conductive collar 1 is in contact with the perforated or incised edges of the peritoneal layer 13. That is, the trocar is positioned such that the conductive collar 1 is surrounded by, and touching, the peripheral edges of the incision or perforation. Then, with the collar so positioned, a radio-frequency generator 14 is connected (as via a wire 18) to a ground plate 16 in contact with the patient's body at a relatively remote location. Next a probe 15, which is connected to the free end of a conductor 17, is moved into position to touch contact 9, thereby connecting the control means 2 with the source of radio-frequency energy. With the other electrode 16 grounded to the patient, the control means 2 is operated to deliver the RF energy to the collar 1.

In practice, the RF energy is delivered in sufficient quantity, and with sufficient intensity, to heat and thereby seal the peripheral edges of the incision or perforation. It has been found that application of RF energy as described above, is substantially effective for reducing the incidence of complications that occur following many surgical procedures within the chest or abdomen. More particularly, it has been found that such application of RF energy is effective for inhibiting the natural tendency of the human body to form connecting bridges (i.e., adhesions) between injured areas within a body cavity.

A mechanical locating means can be placed on the trocar 7 to properly position collar 1 such that good contact is maintained between the collar and the tissue that needs treatment. Such mechanical means can be activated by the surgeon following the abdominal puncture to ensure that the collar is appropriately positioned for treating the peritoneal tissue. The mechanical locating means could comprise, for instance, a retractable stop member which is selectively actuated by the surgeon such that, in its extended position, it can be used to readily position the collar relative to the tissue to be treated.

Preferably, the above-described procedure is accomplished within a few seconds, say three seconds, after creating the surgical intrusion through the peritoneal tissue. Alternatively, treatment can be terminated based upon, for example, the sensing of a predetermined change in the impedance or hydration of the tissue being treated. Other methods for determining the treatment period, such as monitoring the temperature change of the surrounding tissue, may be employed. To implement this latter example, the thermocouple 11 of FIG. 1 is employed for temperature sensing.

When the above-described procedure is practiced within a short time period following surgical intrusion into the peritoneal space, the period during release of tissue growth factors is effectively limited. In other words, prompt practice of the procedure reduces, or eliminates, the release of TGF-β at a newly formed surgical site. That is, the efficacy of the method of the present invention can be explained as being due to providing substantially immediate sealing of the edges of surgically-made puncture or incision site in order to limit the release of healing factors such as TGF-β from the site.

The present invention, as disclosed herein above, provides a system for reducing adhesion formation. While no specific limitation to a biological mechanism of action is intended, it appears probable that the mechanism is related to reducing, or eliminating the release of TGF-β resulting from surgical injury. In any event, actual experimentation on animals has shown that the above-described methods and systems of the present invention are substantially effective in reducing adhesion formation. It is, of course, possible to embody the invention in specific forms other than those described above without departing from the spirit of the present invention. Thus, the above-described embodiment is merely illustrative and should not be considered restrictive in any way.

In another particular embodiment, for example, the invention provides a system for sufficiently sealing the edges of incised or perforated tissue of a peritoneal wall to substantially reduce the incidence of post-surgical adhesions at the surgical site by cooling the tissue sufficiently to inhibit (i.e., reduce) the release of adhesion-producing substances such as growth factors. In practice of this embodiment, cooling is accomplished by applying a low-boiling point liquid substance such as liquid nitrogen, Freon™ or the like to the edges of incised or perforated tissue.

As another example of a particular embodiment, the present invention may provide a system for sufficiently sealing the edges of incised or perforated tissue of a peritoneal wall to substantially reduce the incidence of post-surgical adhesions at the surgical site by applying a sealing substance at the site of injury. The sealing substance would inhibit (i.e., reduce) the release of adhesion-producing substances such as growth factors. In practice of this embodiment, the sealing substance can be a bio-compatible material such as a cyanoacrylate liquid or the like which is applied to the edges of surgical incisions or perforations of the peritoneum tissue. Cyanoacrylates suitable for such uses include the following structures: wherein R is an alkyl or other suitable substituent.

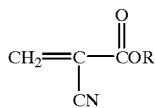

Such cyanoacrylates are disclosed in U.S. Pat. Nos. 3,527,224; 3,591,676; 3,667,472; 3,995,641; 4,035,334; and 4,650,826 which patents are incorporated herein by reference. In addition, it is contemplated that the cyanoacrylate composition employed can optionally comprise a formaldehyde scavenger compound such as those described by Leung, et al., U.S. Pat. No. 5,328,687, which patent is incorporated herein by reference in its entirety. The use of such scavengers has been suggested as enhancing internal in vivo applications of cyanoacrylates by, for example, reducing inflammation associated therewith.

Other sealing materials could be bio-compatible synthetic polyvinyl resins, polylactate glycolides, polycaprolactones, poly oxyethylenes, and other such materials. One could also use biological materials such as proteins like collagen, gelatin, elastin, albumins, and the like, or mixtures thereof.

The method of inhibiting or eliminating adhesion formation can be extended to large surgical incisions (i.e. incisions larger than the laparoscopic incisions) made during open surgery. Again, similar to treating the wound edges created during laparoscopic surgery, the wound edges created during open surgery could be treated, as with heat, to eliminate adhesion formation. In practice, a wide variety of energy sources such as microwave, infrared, ultraviolet, optical (e.g., laser) and mechanical energy (e.g., ultrasound) could be used to generate the necessary heat.

It can now be appreciated that the scope and spirit of the present invention is defined by the appended claims, rather than by the preceding description; therefore, all variations and equivalents which fall within the range of the following claims are intended to be embraced therein.

What is claimed is:

1. A method for treating edges of surgical incisions or perforations of walls of peritoneal or pleural spaces to reduce incidence of post-surgical adhesions, comprising:
   providing a controlled source of energy;
   selectively connecting said source of energy with a conductive surface means for selective placement in contact with edges of an incised or surgically injured peritoneal or pleural tissue;
   placing said surface means in contact with said tissue;
   applying energy to said tissue; and
   altering temperature at said tissue edges sufficiently to reduce the incidence of post-surgical adhesions.

2. A method according to claim 1 wherein the temperature altering step includes applying radio-frequency energy for treating the edges of the incised or surgically injured peritoneal or pleural tissue for reducing the incidence of the post-surgical adhesions.

3. A method for treating edges of surgical incisions or surgically injured peritoneal or pleural tissue for reducing incidence of post-surgical adhesions, comprising:
   placing a sealing device adjacent to the edges of the surgically incised or surgically injured peritoneal or pleural tissue; and
   activating the sealing device for treating the edges of the surgically incised or surgically injured peritoneal or pleural tissue sufficiently to substantially reduce the incidence of the post-surgical adhesions.

4. A method according to claim 3 further comprising the step of generating indicator signal when the tissue edges are treated sufficiently to substantially reduce the incidence of the post-surgical adhesions.

5. A method according to claim 4 wherein said generating step is preceded by sensing a change in impedance of the tissue being treated.

6. A method according to claim 4 wherein said generating step is preceded by sensing a change in hydration of the tissue being treated.

7. A method according to claim 3 wherein the sealing device is activated to provide sufficient electrical energy to cause shrinkage of collagen material adjacent to the sealing means.

8. A method according to claim 3 wherein the sealing device is activated to provide a temperature increase at the sealing means.

9. A method for reducing incidence of post-surgical adhesions around an incision in a human or animal body, the method comprising:
   treating tissue at the incision by applying energy thereto;
   monitoring at least one tissue parameter during said treating; and
   terminating the treating when said tissue parameter reaches a predetermined value indicative of altering release of substances that control adhesion formation.

10. The method according to claim 9, wherein the tissue parameter corresponds to a period of treating the tissue.

11. The method according to claim 9, wherein the tissue parameter is tissue hydration.

12. The method according to claim 9, wherein the tissue parameter is tissue impedance.

13. The method according to claim 9, wherein the tissue parameter is tissue temperature.

14. The method according to claim 9, wherein said treating comprises controlled application of radio-frequency energy.

15. A method for treating tissue during surgery to reduce incidence of post-surgical adhesions, comprising:

making an incision in a patient to form cut tissue edges;

treating the tissue by applying energy to at least a portion of the cut tissue edges sufficient to reduce the incidence of post-surgical adhesions;

monitoring a tissue parameter during said energy application; and terminating energy application based on a predetermined change in said monitored tissue parameter.

16. The method according to claim 15, wherein the treating comprises:

placing at least one electrode adjacent the cut edge of the tissue; and delivering a controlled energy to the cut edge of the tissue through the electrode.

17. A system for reducing post surgical adhesions resulting from perforations of a patient's abdominal wall, comprising:

an elongate member configured and dimensioned to be inserted through the perforation on the abdominal wall;

positioning means to position said elongate member with respect to the abdominal wall;

a conductive element disposed on said elongate member and positioned in cooperation with the positioning means to contact incised edges of the perforation; and an energy source communicating with said conductive element to provide a controlled amount of energy to the conductive element such that energy is applied to the incised tissue edges.

18. The system according to claim 17, further comprising:

a sensor disposed adjacent said conductive element to sense a tissue parameter; and a controller communicating with said sensor and said energy source to terminate energy application when the sensed tissue parameter reaches a value indicative of a reduction in post surgical adhesions.

19. The system according to claim 18, wherein said sensor comprises a thermocouple.

20. The system according to claim 17, wherein said elongate member comprises a trocar.

21. The system according to claim 17, wherein said energy source comprises a radio-frequency generator.

22. The system according to claim 17, wherein said conductive element is formed as a sleeve that surrounds a section of the elongate member.

23. A system for reducing the incidence of post-surgical adhesions, comprising:

a trocar;

a conductive element positioned on said trocar to contact cut tissue edges through which the trocar is placed; and a controlled source of energy communicating with said conductive element to apply energy to the tissue through said conductive element sufficient to reduce the incidence of post surgical adhesions.

24. The system according to claim 23, further comprising:

a sensor disposed on said trocar adjacent the conductive element for sensing a tissue parameter; and a controller communicating with said sensor and energy source to control and terminate application of energy in response to a predetermined change in the sensed tissue parameter.

25. The system according to claim 24, wherein said sensor comprises a thermocouple.

26. The system according to claim 23, wherein said controlled energy source is a radio-frequency generator.

27. The system according to claim 23, wherein said trocar includes tissue positioning means.

\* \* \* \* \*